US011826133B2

(12) United States Patent
Huang

(10) Patent No.: US 11,826,133 B2
(45) Date of Patent: Nov. 28, 2023

(54) METHOD AND SYSTEM FOR DETERMINING BRAIN-STATE DEPENDENT FUNCTIONAL AREAS OF UNITARY POOLED ACTIVITY AND ASSOCIATED DYNAMIC NETWORKS WITH FUNCTIONAL MAGNETIC RESONANCE IMAGING

(71) Applicant: BOARD OF TRUSTEES OF MICHIGAN STATE UNIVERSITY, East Lansing, MI (US)

(72) Inventor: Jie Huang, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 346 days.

(21) Appl. No.: 16/489,512

(22) PCT Filed: Feb. 27, 2018

(86) PCT No.: PCT/US2018/019819
§ 371 (c)(1),
(2) Date: Aug. 28, 2019

(87) PCT Pub. No.: WO2018/160512
PCT Pub. Date: Sep. 7, 2018

(65) Prior Publication Data
US 2020/0069237 A1 Mar. 5, 2020

Related U.S. Application Data

(60) Provisional application No. 62/464,413, filed on Feb. 28, 2017.

(51) Int. Cl.
*A61B 5/055* (2006.01)
*G06T 7/11* (2017.01)
(Continued)

(52) U.S. Cl.
CPC .......... *A61B 5/055* (2013.01); *A61B 5/14542* (2013.01); *A61B 5/4064* (2013.01);
(Continued)

(58) Field of Classification Search
CPC .... A61B 5/00; A61B 5/04; A61B 5/05; A61B 5/055; A61B 8/00; A61B 8/08;
(Continued)

(56) References Cited

U.S. PATENT DOCUMENTS

| 2004/0096395 A1 | 5/2004 | Xiong et al. |
| 2011/0046473 A1 | 2/2011 | Pradeep et al. |

(Continued)

FOREIGN PATENT DOCUMENTS

CN    101292871 B  *  4/2007  ............. A61B 5/055

OTHER PUBLICATIONS

Monir et al. 2011 IEEE 8th ICICSP 5 pages (Year: 2011).*
(Continued)

*Primary Examiner* — Christopher Koharski
*Assistant Examiner* — Patrick M Mehl
(74) *Attorney, Agent, or Firm* — Harness, Dickey & Pierce, PLC

(57) ABSTRACT

A method for identifying brain-state dependent functional areas of unitary pooled activity (FAUPAs) using a statistical model that does not require a priori knowledge of the activity-induced ideal response signal time course is provided. A system for identifying a functional network in a brain of a living object includes a FAUPA identifier configured to identify FAUPAs by analyzing a plurality of images of the brain over a predetermined period. The plurality of images include a plurality of voxels, and the FAUPA identifier analyzes each voxel of the plurality of voxels in relation to one or more surrounding voxels of each voxel until each voxel of the plurality of voxels is evaluated. A
(Continued)

brain network identification module configured to construct the functional network based on the identified FAUPAs that are functionally connected. A display module configured to display images of the brain depicting the FAUPAs included in the functional network.

10 Claims, 14 Drawing Sheets

(51) Int. Cl.
  *A61B 5/145*    (2006.01)
  *A61B 5/00*    (2006.01)
  *G06T 7/00*    (2017.01)

(52) U.S. Cl.
  CPC .............. *G06T 7/0016* (2013.01); *G06T 7/11* (2017.01); *A61B 5/742* (2013.01); *A61B 2576/026* (2013.01)

(58) Field of Classification Search
  CPC ..... A61B 5/04004; A61B 5/40; A61B 5/4058; A61B 5/72; A61B 5/7203; A61B 5/7207; A61B 5/7221; A61B 5/7264; A61B 5/7275; A61B 5/742; A61B 6/027; A61B 8/0808; A61B 5/4064; A61B 5/14542; A61B 2576/026; G06K 9/00; G06K 9/62; G06K 9/6202; G06K 9/621; G06K 2009/6213; G06K 9/0053; G06K 9/00536; G06T 7/11; G06T 7/0016; G16H 30/40

See application file for complete search history.

(56) References Cited

U.S. PATENT DOCUMENTS

| | | |
|---|---|---|
| 2011/0188722 A1 | 8/2011 | Huang |
| 2012/0083688 A1 | 4/2012 | Nauman et al. |
| 2013/0184558 A1 | 7/2013 | Gallant et al. |
| 2013/0245424 A1 | 9/2013 | deCharms |
| 2014/0343399 A1 | 11/2014 | Posse |
| 2015/0272468 A1 | 10/2015 | Liu et al. |
| 2015/0272469 A1 | 10/2015 | Fox et al. |
| 2016/0113501 A1* | 4/2016 | Hua ................... A61B 5/0042 600/420 |
| 2016/0284082 A1* | 9/2016 | Varkuti ................. A61B 6/037 |

OTHER PUBLICATIONS

Gonzalez-Castillo et al. 2014 Frontiers in Neuroscience 8:1-19 (Year: 2014).*
Lu et al. 2003 NeuroImage 20:455-465 (Year: 2003).*
Sankowski et al. 2009 Proc SPIE 7502 Photonics Applications in Astronomy Communications Industry High Energy Physics Exp 2009 75022M 9 pages (Year: 2009).*

* cited by examiner

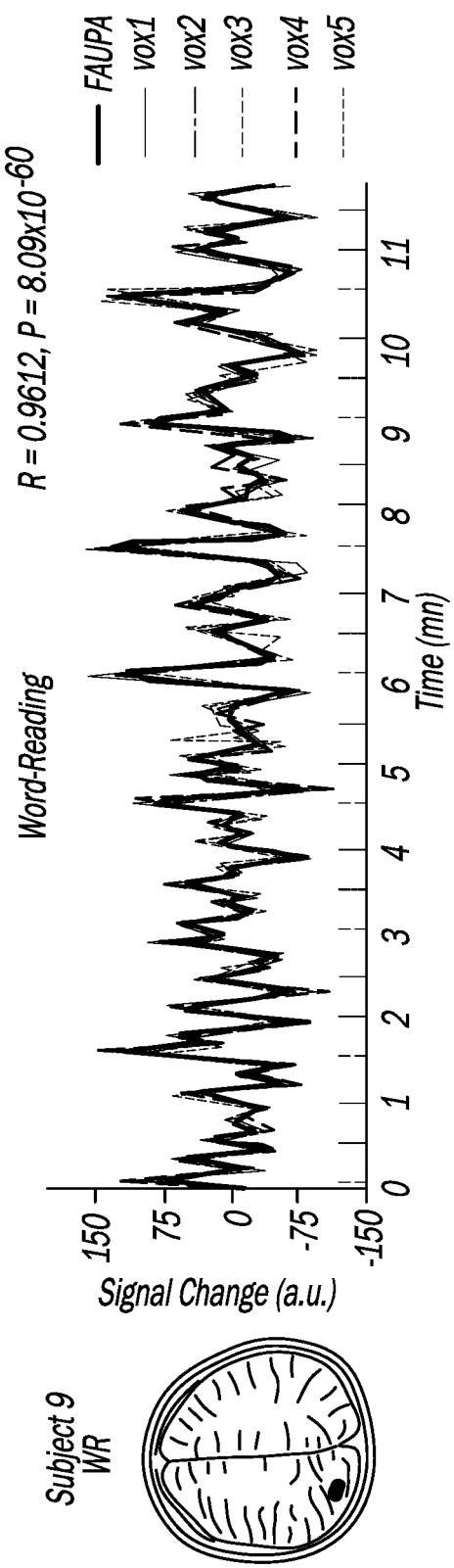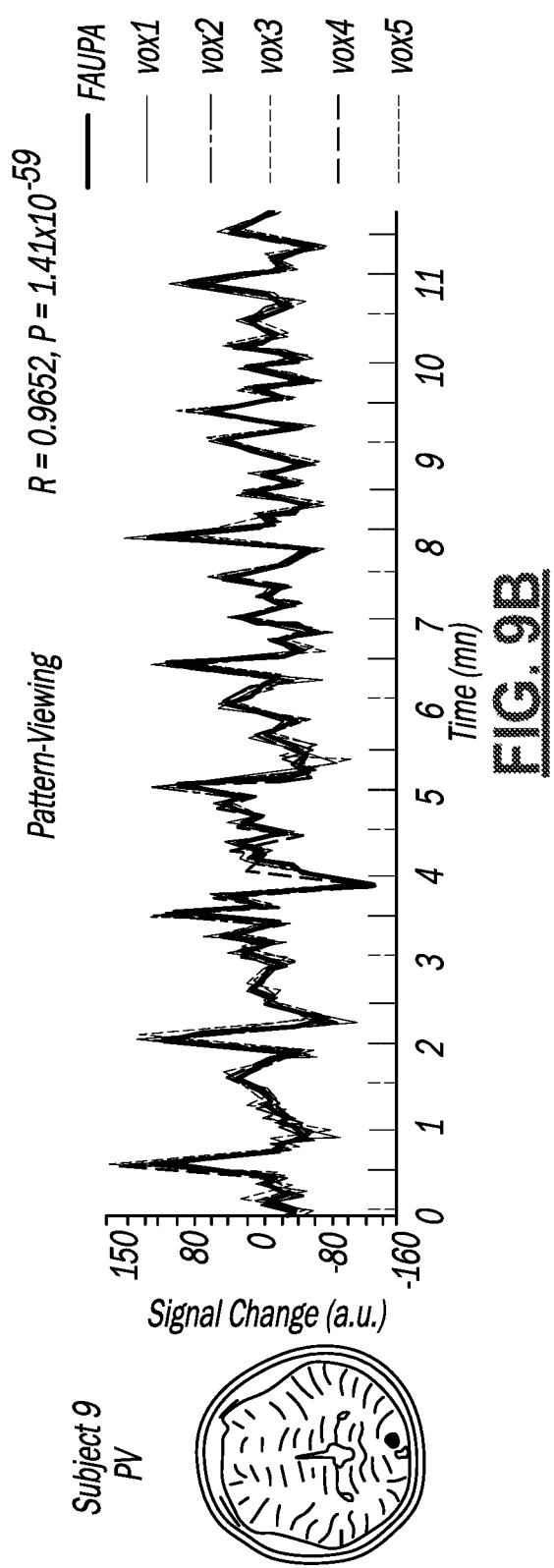

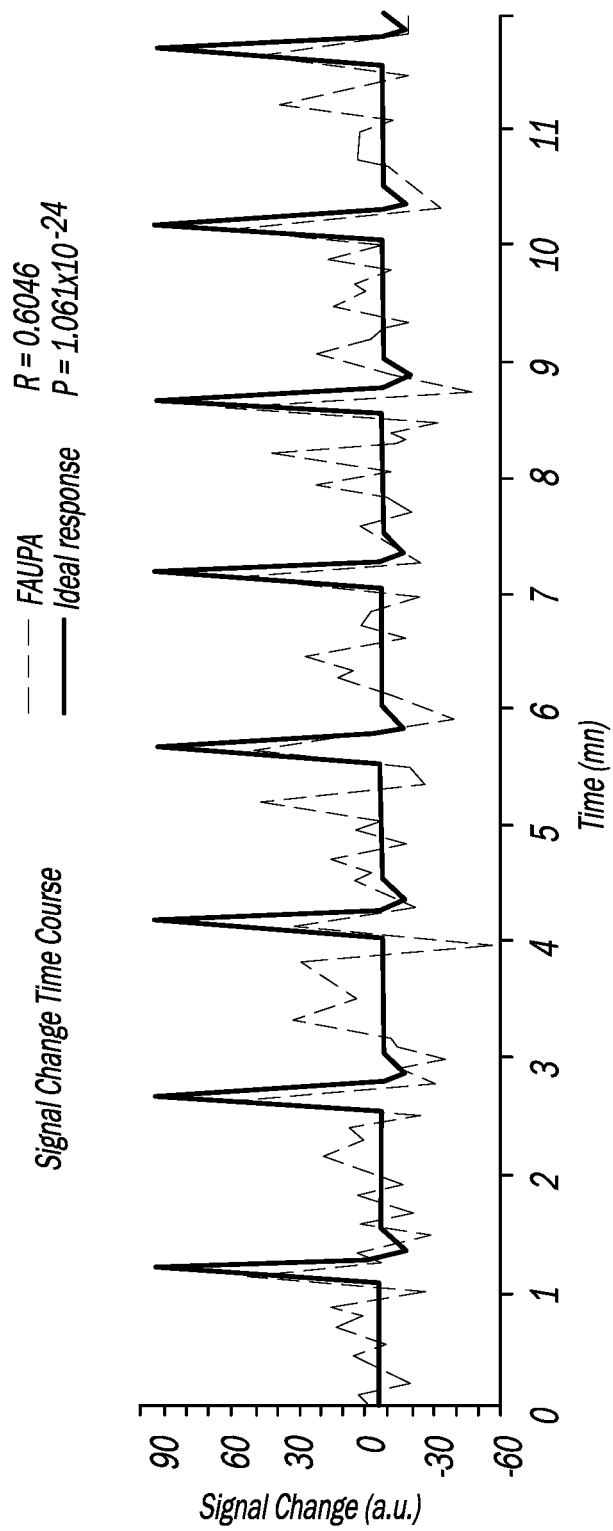

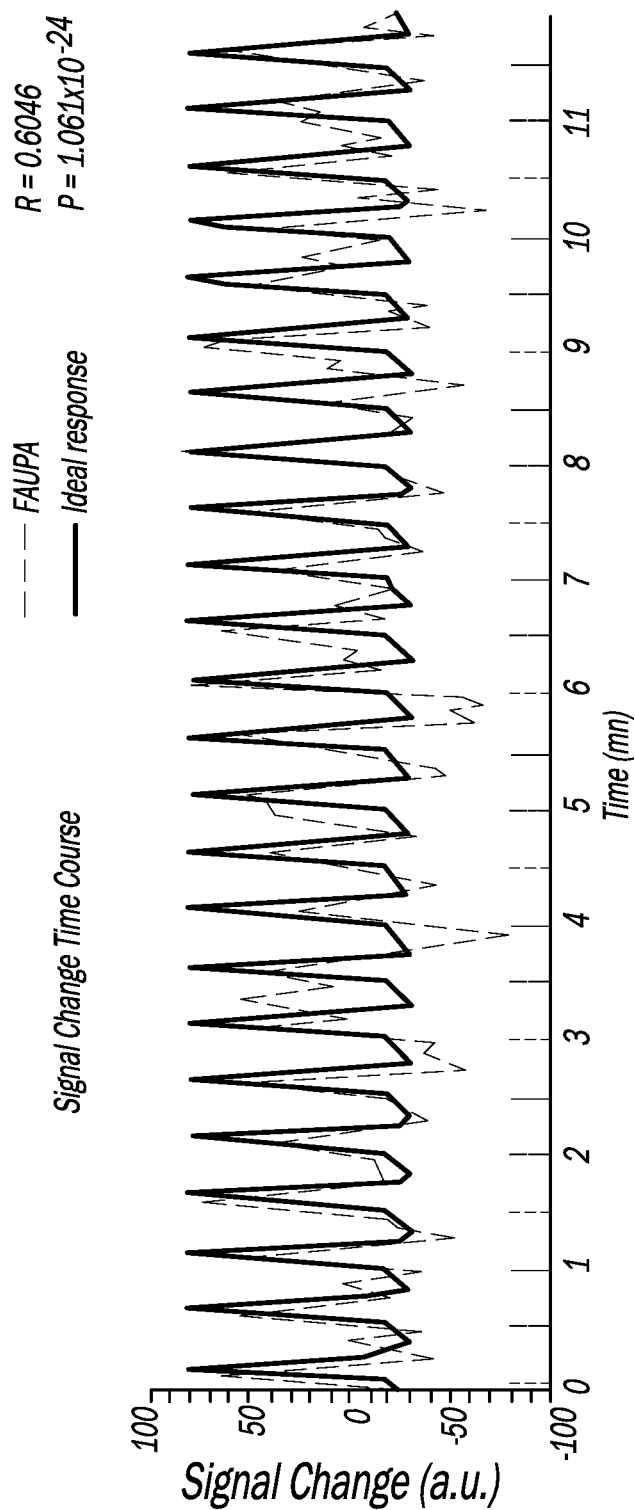

METHOD AND SYSTEM FOR DETERMINING BRAIN-STATE DEPENDENT FUNCTIONAL AREAS OF UNITARY POOLED ACTIVITY AND ASSOCIATED DYNAMIC NETWORKS WITH FUNCTIONAL MAGNETIC RESONANCE IMAGING

CROSS-REFERENCE TO RELATED APPLICATIONS

This application is a National Phase Entry of International Patent Application No. PCT/US2018/019819, filed on Feb. 27, 2018, which claims the benefit of U.S. Provisional Application No. 62/464413, filed Feb. 28, 2017. The entire disclosure of the applications referenced above are incorporated by reference.

FIELD

The present disclosure relates to detecting neural activity in a living object using functional magnetic resonance imaging.

BACKGROUND AND SUMMARY

This section provides background information related to the present disclosure which is not necessarily prior art.

Magnetic resonance imaging (MRI) is an imaging technique where the presence of hydrogen atoms, which occur at different densities in fat, water, bone, air, etc., is three-dimensionally mapped in a patient. MRI technology has seen tremendous success as a non-invasive diagnostic tool for many conditions, such as blood clots and tumors.

Non-invasive blood oxygenation level dependent (BOLD) functional magnetic resonance imaging (fMRI) technique has evolved as a major neuroimaging tool for studying human brain functional organization at large-scale neural activity. This is achieved by monitoring the relative levels of oxygenated and deoxygenated hemoglobin within the blood in the brain, which is directly related to the oxygen consumption from neurons, known as the hemodynamic response function (HRF). The relative levels of oxygenated and deoxygenated hemoglobin can be monitored as the oxygenated hemoglobin has different magnetic properties from the deoxygenated hemoglobin. This affect is observed because neurons do not store glucose in their cells and require increased blood flow to bring energy (glucose and oxygen) to the active neurons. When the neuron activity is decreased, the blood flow returns to normal and the hemodynamic response returns to steady state.

In fMRI, multiple images of the brain, roughly 100-2,000, are taken and the signal strength in each voxel (small region of brain volume) is compared over time. Due to the amount of noise in the signal, and also due to the massive amount of data, statistical algorithms are employed to analyze the data and filter between noise, steady state brain function, and enhanced brain function. Images in which functional connectivity and enhanced brain activity are highlighted during the resting state and task state of the patient can then be generated.

Due to its statistical nature, the accuracy of fMRI analysis can be an issue. In particular, an assumption made in many models, including popular GLM model, is that the HRF shape is known. This leads to issues as the assumption of the HRF shape is what filters out meaningful neuron activity from that of physiological noise, and incorrect assumptions lead to false readings. Models such as finite impulse response (FIR) have been developed which allow for an arbitrary estimation of the HRF for each voxel to combat this problem. Another issue arising from current statistical models is the existence of spatial autocorrelation issues, where autocorrelation affects assumed to be a Gaussian shape, but in reality possess long tails.

In accordance with the present disclosure, a method and system for determining brain-state dependent functional areas of unitary pooled activity are provided. The functional areas of unitary pooled activity (FAUPAs) are identified based on a statistical model that is executed by a controller using images taken from an fMRI scanner. As described herein, the system for identifying FAUPAs does not require a priori knowledge of the activity-induced ideal response signal time course.

DRAWINGS

The drawings described herein are for illustrative purposes only of selected embodiments and not all possible implementations, and are not intended to limit the scope of the present disclosure.

Figure 9C:
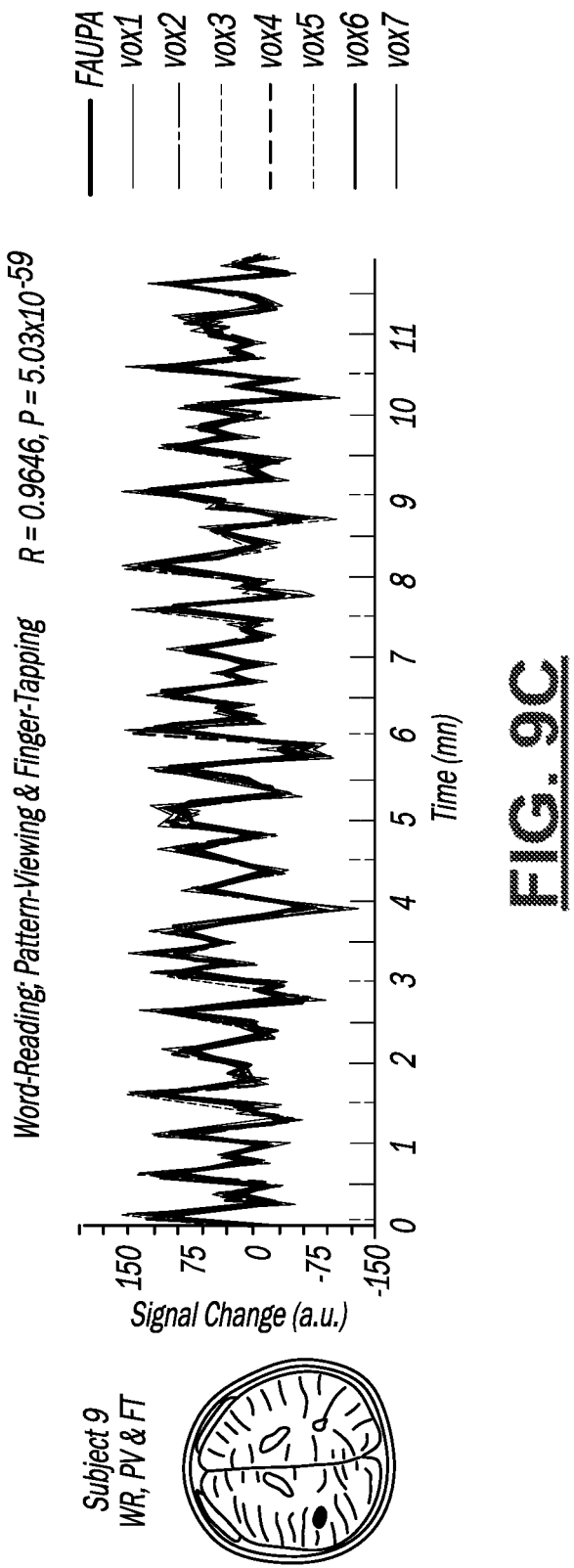

FIGS. 9A, 9B, and 9C illustrate expected test results for three specific task-associated FAUPAs from the task study for a test subject; and FIGS. 10A, 10B, 10C, and 10D are graphs illustrating the temporal correlation of task-associated signals change time course with the task-induced ideal response signal change time course for different tasks.

DETAILED DESCRIPTION

The present disclosure describes the detection of a functional area of unitary pooled activity (FAUPA) within the brain using BOLD signals. A FAUPA is defined as an area in which the pooled activity is a dynamically unitary activity or, in other words, an area of the brain in which the temporal variation is the same across the entire area. This unitary activity implies a perfect temporal correlation everywhere for the activity-induced BOLD response. Specifically, in the FAUPA, the Pearson correlation coefficient (R) is equal to 1. When a FAUPA is measured with fMRI, the voxelwise signal time course is no longer perfectly correlated among each other due to noise. Computing the temporal correlation of its mean signal time course with a voxel's signal time course yields a Pearson correlation coefficient for each voxel, and the mean and standard deviation of these Pearson correlation coefficients can be used to establish a statistical model to determine the FAUPA.

The basis for FAUPA is derived from activity-induced BOLD response. Specifically, with n(r,t) representing a pooled activity, where r is the spatial location and t is the time, the corresponding activity-induced BOLD response S(r,t) of equation 1 may be described as the convolution of n(r,t) with a hemodynamic response function h(t). The temporal variation of the pooled activity is the same everywhere and, therefore, n(r,t)=f(r)·g(t), where g(t) denotes the temporal variation and f(r) represents the spatial variation across the area. This implies the pooled activity is spatially coherent and temporally synchronized. Accordingly, the activity-induced BOLD response is reduced to equation 2 in which G(t) is a generic time function characterizing the temporal variation of the BOLD response.

$$S(r, t) = \int_0^t n(r, \tau) \cdot h(t-\tau) \cdot d\tau \quad \text{Equation 1}$$

$$S(r, t) = f(r) \cdot G(t), \text{ where } G(t) = \int_0^t g(\tau) \cdot h(t-\tau) \cdot d\tau \quad \text{Equation 2}$$

For a given two positions, $r_1$ and $r_2$, the corresponding two BOLD responses are $S_1(r_1,t)=f(r_1) \cdot G(t)$ and $S_2(r_2,t)=f(r_2) \cdot G(t)$, respectively. Since $S_1$ and $S_2$ have identical temporal variation, the temporal correlation between $S_1$ and $S_2$ is one (i.e., the Pearson correlation coefficient (R) is 1). This is also true for any two positions, showing a perfect temporal correlation of the BOLD response everywhere in the FAUPA.

When the FAUPA is measured with fMRI, the voxelwise signal time course is $S_i(t)=C_i \cdot G(t)+\delta_i(t)$, where $C_i$ is the coefficient for the ith voxel and $\delta_i(t)$ denotes the physiological and instrumental noises. In an ideal situation without any physiological and instrumental noises (i.e., $\delta_i(t)=0$), the temporal correlation of $S_i(t)$ is perfect among all of these voxels. The FAUPA's signal time course $\overline{S}(t)$ is then defined as the mean of $S_i(t)$, and is defined by equation 3, where N denotes the total number of voxels contained in the FAUPA.

$$\overline{S}(t) = \frac{1}{N} \sum_{i=1}^{N} S_i(t) \quad \text{Equation 3}$$

The correlation coefficient of $\overline{S}(t)$ with $S_i(t)$ as $R_i$, and the FAUPA's $\overline{R}$ is defined as the mean of $R_i$. When $\delta_i(t)=0$, $\overline{S}(t)=\overline{C} \cdot G(t)$, where $\overline{C}$ is the mean of $C_i$. This results in $R_i=1$ for every voxel and, consequently, $\overline{R}=1$, reflecting the dynamically unitary pooled activity. Practically, there is some physiological and instrumental noise (i.e., $\delta_i(t) \neq 0$) and, therefore, the mean (μ) and standard deviation (σ) of the Pearson correlation ($R_i$) are used to measure the overall strength of the correlation and its corresponding variation among the voxels, respectively. As described further below, the mean and standard deviation are calculated and used by a brain activity detection device having a processor to establish a statistical model for determining the FAUPA.

Figure 1:
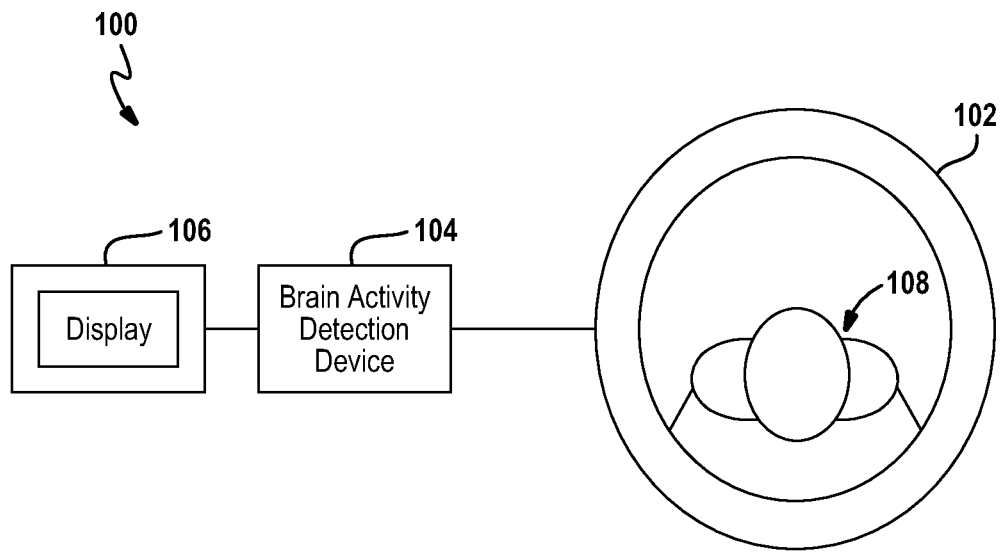
FIG. 1 illustrates a system for detecting brain activity using an fMRI scanner and a brain activity detection device of the present disclosure.
Figure 2:
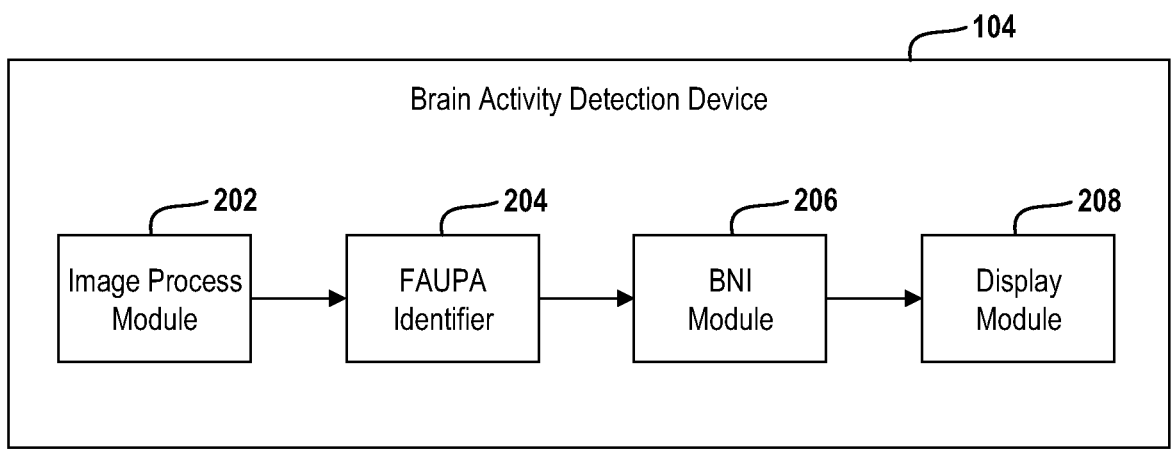
FIG. 2 is a block diagram of the brain activity detection device.

FIGS. 1 and 2 illustrate an fMRI system 100 that detects brain activity of a living subject, such as a human, by identifying FAUPA within the brain. The system 100 includes a functional magnetic resonance imaging (fMRI) scanner 102, a brain activity detection device 104, and a display 106. The fMRI scanner 102 captures functional neuroimages of a living subject 108 within a predetermined time period defined by an operator. The fMRI scanner 102 may include a magnet, shim coils, and gradient coils, as well as appropriate elements for supporting a human or other animal subject to be imaged. The images from the fMRI scanner 102 are in units of voxels and capture the change in blood flow or, in other words, the hemodynamic response related to energy use by brain cells.

Utilizing the images captured, the brain activity detection device 104 executes a series of processes to identify FAUPAs and networks in the brain based on the identified FAUPAs. The brain activity detection device 104 may include a controller that has a memory for storing the series of processes as computer executable instructions and a processor for executing the instructions. The processor performs various computational steps disclosed herein. It is understood that the processor does not have to perform all of the computational steps and that the operator may perform certain steps, especially when the experience of the operator is necessary to make a subjective assessment or modification to a calculation.

The operator may control the system 100, such as the fMRI scanner 102 and the computation performed by the brain activity detection device 104 via a user interface (not shown). The user interface provides the operator with the ability to receive, input, or manipulate information from the fMRI system 100. For example, the user interface for input and manipulation can include a keyboard, mouse, roller ball, touch screen, etc., through which the operator can make the various parameter selections required. It is understood that the user interface can also include peripheral equipment through which the computer communicates with the operator.

The display 106 is communicably coupled to the brain activity detection device 104 and provides a visual output from the detection device 104. For example, the visual output provided on the display 106 may include images of the subject's brain with one or more highlighted regions of interest, a graphical representation of the time course signal over time, and/or other suitable results. The display 106 may be a monitor, such as liquid crystal display, and can be coupled to the detection device 104 via wireless and/or wired communication links.

In an example embodiment, the brain activity detection device 104 includes an image process module 202, a FAUPA identifier 204, a brain network identification (BNI) module 206, and a display module 208. The image process module 202 refines the functional images by executing analysis of functional neuroimages (AFNI) programs. For example, the AFNI programs include: (1) a 3dDespike routine for removing spikes from the signal intensity time course; (2) a 3dTshift routine for slice-timing correction of the image acquisition time difference from slice to slice; (3) a 3dvolreg routine for correcting motion of the images to align all volume images from the functional scans to the very first volume images of the very first functional scan; (4) a 3dBandpass routine for bandpassing the signal intensity time course to the range of 0.009 Hz 0.08 Hz, etc. These programs are stored in the memory of the brain activity detection device 104 and executed by the processor.

The FAUPA identifier 204 is based on a statistical model to determine FAUPAs in the brain. More specifically, the identifier 204 analyzes each voxel in relation with one or more surrounding voxels until all voxels are evaluated. For each group, the identifier 204 determines (1) if the group of voxels which includes the selected voxel is a stable region, and then, if the group is stable, (2) whether the region is a FAUPA. A detailed explanation of the FAUPA identifier 204 is described below with reference to FIGS. 4 and 5.

Using the identified FAUPA, the BNI module 206 constructs one or more networks that identify active areas of the brain in association with the behavior of the subject. For example, the BNI module 206 is configured to identify a functional connectivity map, and a task related neural network. The functional connectivity map illustrates areas of the brain that are functionally connected to each other, and the task related neural network associates a task being performed by the subject during the imaging process with the identified FAUPA. To determine the functional connectivity map, the BNI module 206 uses the mean signal time course of an identified FAUPA to calculate the correlation coefficient of the FAUPA with each voxel signal time course for the entire brain, and then compares the correlation coefficient with a threshold value (e.g., R=0.5). The resulting regions are identified as being functionally connected. For the task related neural network, during the imaging process, the operator directs the subject to perform a specific task or activity at a predetermined interval throughout the time period of imaging. A region identified as a task-associated FAUPA is a dynamic region that is provoked by tasks performed by the subject and the provoked-activity is the same across the entire region. Therefore, one or more task-associated FAUPAs identified at the time the subject performs the task are identified as part of a neural network for the particular task and one or more task-associated FAUPAs identified during the performance of the task are designated as areas within the brain that are functionally connected (i.e., task associated network). In an example embodiment, the brain activity detection device 104 includes a series of algorithms that are stored in the memory and executed by the processor to identify the functional connectivity map and the task related neural network. In addition, the operator may change the requirements for identifying the various networks by operating the brain activity detection device 104 via the user interface. While the present disclosure describes specific networks identifiable by the BNI module 206, it should be readily understood that the BNI module 206 may be configured to identify other networks using the identified FAUPAs, and should not be limited to the examples provided herein.

The display module 208 generates visual outputs and displays the outputs by way of the display 104. The visual outputs may include images of the brain that highlight the networks identified by the BNI module 206 and/or graphical representations of the signals over time. The images may also highlight networks based on the FAUPA.

A detailed explanation of the processes executed by the brain activity detection device 104 to identify FAUPAs and generate one or more visual outputs is now provided. The brain activity detection device 104 stores one or more software programs that perform the operations described herein with reference to FIGS. 3-5 when the software programs are executed by the processor. The brain activity detection device 104 may execute the processes described herein in response to receiving image from the fMRI scanner or based on a command from the operator via the user interface.

Figure 3:
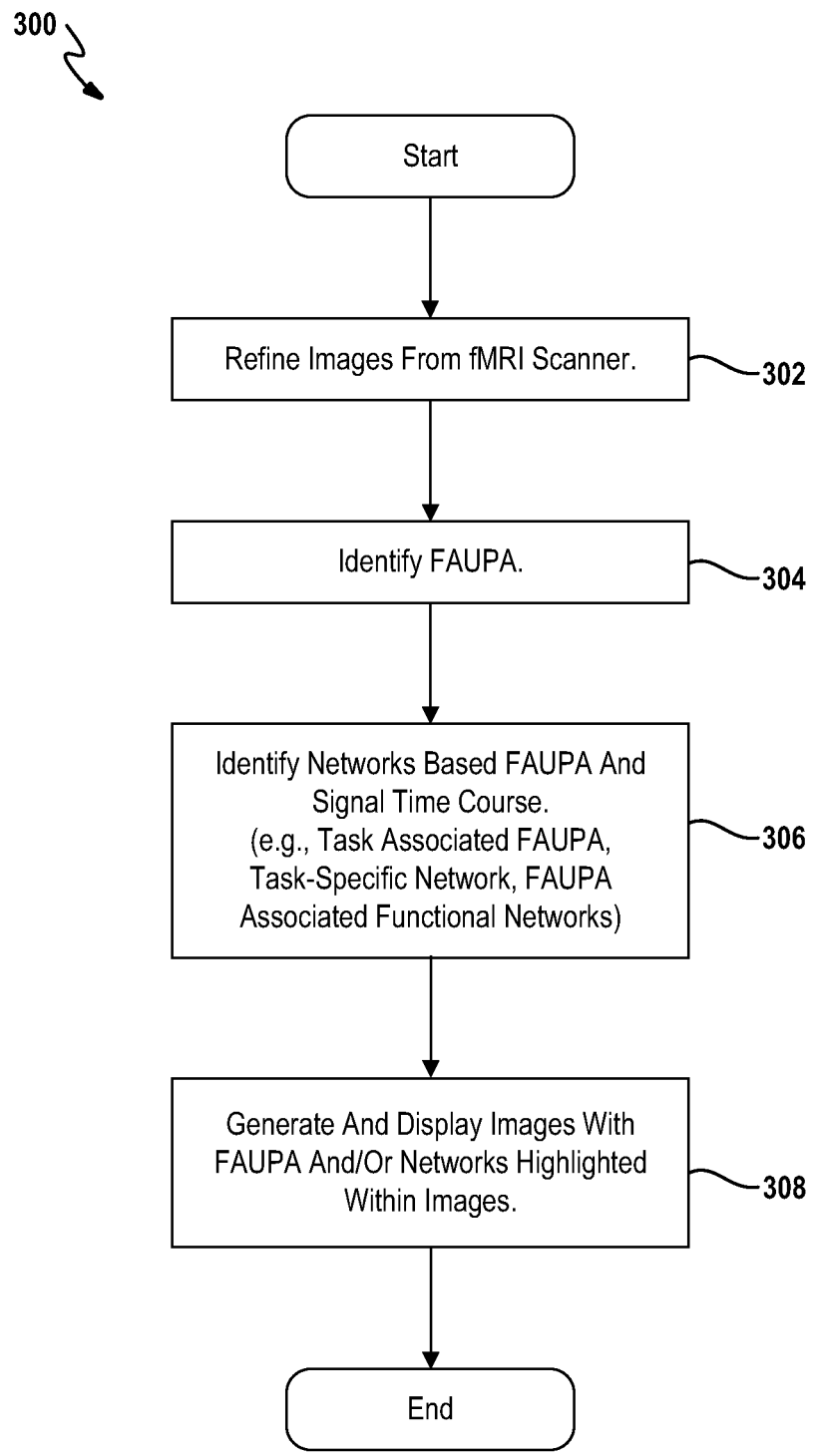
FIG. 3 is a flowchart of a brain activity detection routine.

FIG. 3 is a flowchart of a brain activity detection routine 300 that performed by the brain activity detection device 104. At 302, the brain activity detection device 104 operates as the image process module 202 to refine the images from the fMRI scanner 102 by executing one or more programs, such as the AFNI programs described above.

Figure 4:
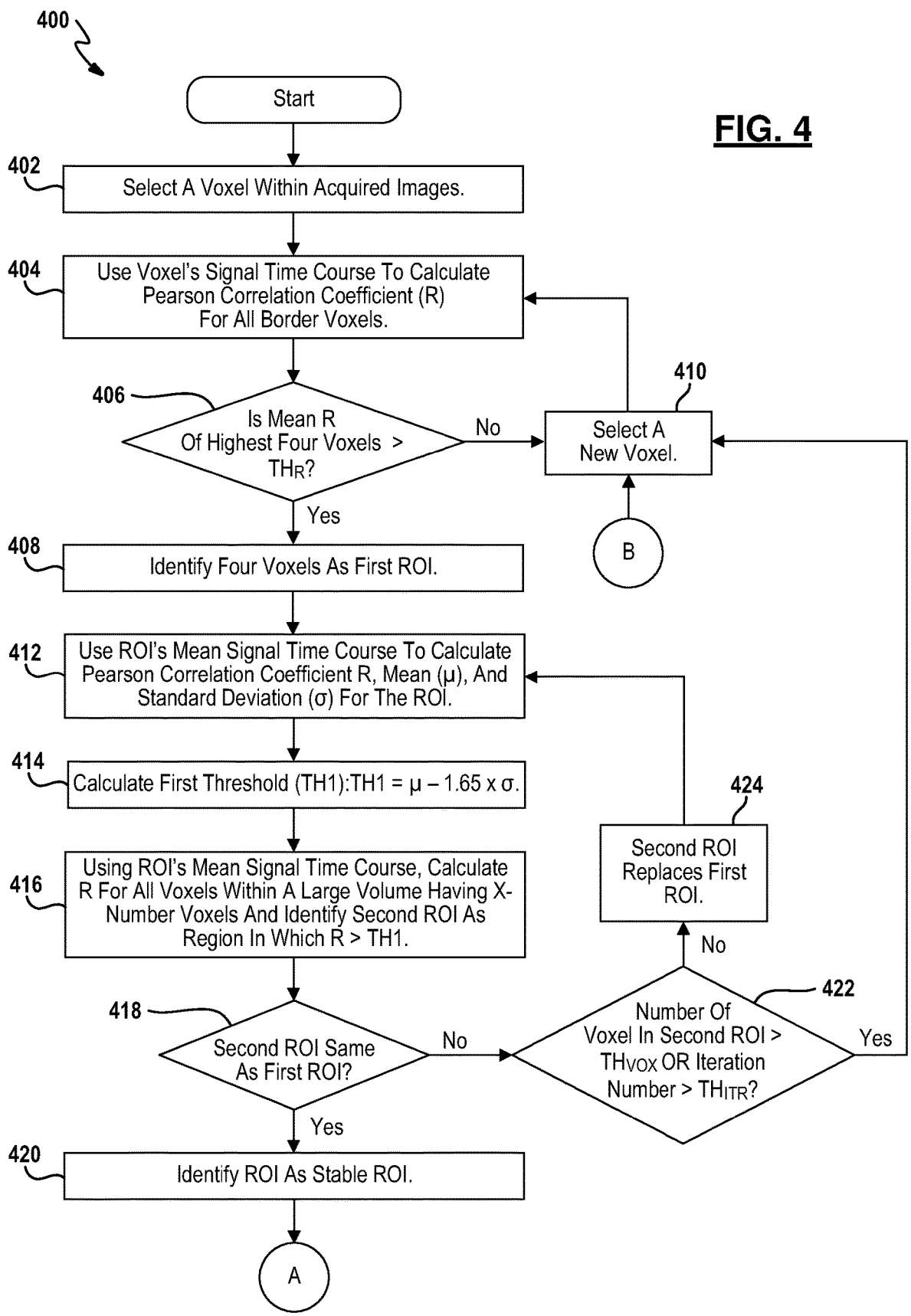
FIGS. 4 and 5 are flowcharts of a functional area of unitary pooled activity (FAUPA) identification routine.
Figure 5:
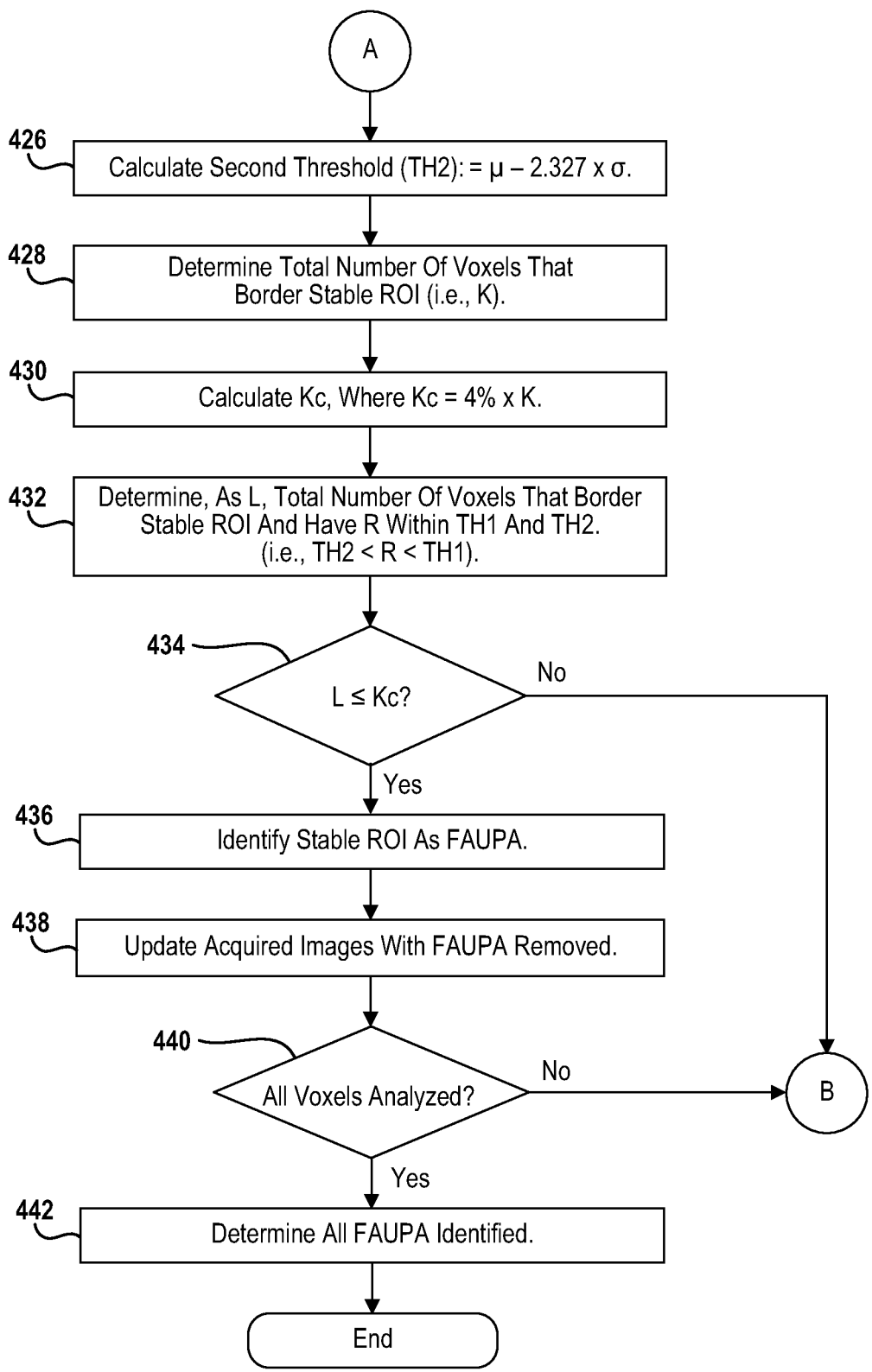

After refining the images, the brain activity detection device 104 operates as the FAUPA identifier 204 and identifies FAUPAs within the brain by executing a FAUPA identification routine 400 provided in FIGS. 4 and 5. Accordingly, at 304, the device 104 proceeds to the routine 400 to select a single voxel within the images and to calculate the Pearson correlation coefficient (R) for voxels bordering the selected voxels based on the time course signal of the voxel (S(t)), at 402 and 404.

At 406, the device 104 determines whether the mean Pearson correlation coefficient of four voxels is greater than a Pearson correlation coefficient threshold ($TH_R$). Specifically, from among the selected voxel and the surrounding voxels, the device 104 selects four voxels that have the highest Pearson correlation coefficient and determines the mean Pearson correlation coefficient ($\bar{R}$). At 406, $\bar{R}$ is compared to $TH_R$ (e.g., 0.9) and, if the mean Pearson correlation coefficient is greater than the threshold, the device 104 designates the four voxels as a first region of interest (ROI), at 408. If $\bar{R}$ is less than $TH_R$, the device 104 selects a new voxel in the image, at 410, and the routine returns to 402. As discussed above, for an activity induced BOLD response (S(t)) in a FAUPA, the temporal correlation is assumed to be perfect for the BOLD responses at two adjacent voxels and, therefore, the Pearson correlation coefficient (R) should be close to 1.

At 412, the device 104 calculates, based on a mean signal time course of the first ROI, the Pearson correlation coefficient (R), the mean ($\mu$), and the standard deviation ($\sigma$) for the first ROI. Then, using the mean ($\mu$) and the standard deviation ($\sigma$), the device 104 calculates a first threshold (TH1), as TH1=$\mu$−1.65 $\sigma$, at 414.

From the first ROI, the device 104 selects a larger region having X-number of voxels (e.g., 11×11×11 region) and, using the mean signal time course of the first ROI, calculates the Pearson correlation coefficient (R) for all of the voxels within the larger region. The second ROI is formed at 416 where the largest cluster with all voxels connected to each other and each voxel has a Pearson correlation coefficient (R) greater than the first threshold (TH1).

At 418, the device 104 determines if the second ROI is the same as the first ROI. If the first ROI and the second ROI are the same, the ROI is identified as a stable ROI, at 420, and the device continues to 426 of FIG. 5. If they are different, the device 104, at 422, determines if the number of voxels in the second ROI is greater than the voxel threshold ($TH_{VOX}$), such as 29 voxels, or if the number of iteration is greater than an iteration threshold ($TH_{ITR}$), such as 20. For determining the number of iterations, the device 104 may have a counter or register that tracks that number of times the device 104 determines if the second ROI is equal to the first ROI for a selected voxel. If either of the conditions is met, the device returns to 410 to select a new voxel. If none of the conditions are met, the device 104 identifies the second ROI as the first ROI, at 424, and returns to 412.

Referring to FIG. 5, the device 104 calculates a second threshold (TH2) as TH2=$\mu$−2.327$\sigma$, at 426. The device 104 then determines the total number of voxels that border that stable ROI (i.e., K) and uses the total number of voxels to calculate a voxel criteria (Kc), which is a certain amount (e.g., 4%) of the total number of voxels that border the stable ROI (i.e., Kc=4%×K), at 428 and 430. The amount of K for determining Kc is not limited to 4% and can be another suitable value.

At 432, the device 104 then determines the total number of voxels that border the stable ROI and that have a Pearson correlation coefficient within the first and second threshold (i.e., TH2<R<TH1) as "L." The device 104 determines if the total number of voxels that border the stable ROI and that have a Pearson correlation coefficient within the first and second thresholds is less than the voxel criteria (i.e., L≤Kc), at 434. If it is true, then the stable ROI satisfies the statistical criterion and is identified as a FAUPA, at 436. Otherwise, the ROI is discarded and the device returns to 410 to select another voxel. From 436, the device 104 removes the FAUPA from the images, at 438, and determines if all of the voxels are analyzed at 440. If all of the voxels are analyzed, the device 104 determines that all of the FAUPAs are identified at 442, the routine 400 ends, and the device 104 returns to the routine 300. If there are some voxels that still need to be analyzed, the device 104 returns to 410 and selects the next voxel.

With all of the FAUPAs identified, the device 104 operates as the BNI module 206 to identify neural networks within the brain and as the display module 208 to generate and display the visual output (i.e., results) via the display 106, at 306 and 308, respectively. The visual outputs may include, for example, images of the brain with the FAUPAs highlighted, graphical representations of the BOLD signal over time, and/or images of one or more neural networks identified.

In the FAUPA identification routine, specific values were provided for certain parameters and/or thresholds. It should be readily understood that the thresholds and parameters may be set at other values and should not be limited to the values provided herein. For example, in step 406, the routine is described as selecting four voxels (e.g., parameter) that have a Pearson correlation coefficient greater than the Pearson correlation coefficient threshold ($TH_R$). In lieu of four voxels, the device may be configured to select 3, 5, or another suitable number of voxels, and should not be limited to four. Similarly, the value for the Pearson correlation coefficient threshold ($TH_R$) should not be limited to 0.9, and can be set to other suitable values, such as 0.88 or 0.92. As another example, in determining the threshold TH1, the standard deviation is multiplied by a factor to account for 95% where p=5% of the one-tail probability for R<TH1.

Alternatively, in determining the threshold TH2, the standard deviation is multiplied by a factor to account for 99% where p=1% for R<TH2. For instance, for calculating TH1 and TH2, the standard deviation is multiplied by 1.65 and 2.327, respectively. These factors can be adjusted (i.e., increased or decreased), but should be close to the preferred value of 1.65 for TH1 and 2.327 for TH2.

To confirm the brain activity detection routine and, more particularly, the statistical method for identifying FAUPAs, two studies were conducted by the inventor. In the first study, FAUPAs were identified for subjects that were requested to be in a resting state during the fMRI scan. In particular, nine subjects were scanned for 12 minutes during which they were instructed to keep their eyes closed and to try not to think about anything but to remain awake. This study is referred to as the resting-state study. In the second study, FAUPAs were identified for the same subjects, who were requested to perform a series of tasks. Specifically, the nine subjects were scanned for 12 minutes during which they were instructed to perform three different tasks: (1) read words silently, (2) passively view patterns, and (3) quickly tap the right-hand five fingers. Each task was performed for six seconds followed by 24 seconds of rest between each task, and this was repeated eight times. This study is referred to as the task study.

The expected results of the two studies are presented in Table 1 shown below. For each subject, the number of FAUPAs, the maximum Pearson correlation coefficient, the minimum Pearson correlation coefficient, the mean ($\mu$), and the standard deviation ($\sigma$) of the Pearson correlation coefficient were determined. For the resting-state study, FAUPAs were detected for each of the nine subjects, and the total number of the identified FAUPAs across the whole brain varied from 121 to 767 with $\mu\pm\sigma=354\pm211$. The mean of the Pearson correlation coefficient ranged from 0.950 to 0.959 for the nine subjects, and the group $\mu$ and $\sigma$ of these mean values were 0.955±0.003, showing an almost perfect temporal correlation within each FAUPA.

TABLE 1

EXPECTED RESULTS OF RESTING-STATE & TASK STUDIES

| | | Resting-State Study | | | | Task Study | | | | |
|---|---|---|---|---|---|---|---|---|---|---|
| | | Pearson Correlation Coefficient R | | | | | Pearson Correlation Coefficient R | | | |
| Subj | FAUPA # | Max | Min | $\mu$ | $\sigma$ | FAUPA # | Max | Min | $\mu$ | $\sigma$ |
| 1 | 228 | 0.991 | 0.909 | 0.957 | 0.014 | 63 | 0.980 | 0.897 | 0.951 | 0.016 |
| 2 | 374 | 0.992 | 0.915 | 0.959 | 0.015 | 135 | 0.983 | 0.892 | 0.951 | 0.017 |
| 3 | 540 | 0.992 | 0.882 | 0.954 | 0.015 | 166 | 0.985 | 0.919 | 0.954 | 0.013 |
| 4 | 207 | 0.991 | 0.905 | 0.953 | 0.014 | 68 | 1 | 0.867 | 0.952 | 0.019 |
| 5 | 435 | 0.990 | 0.897 | 0.954 | 0.016 | 201 | 0.987 | 0.889 | 0.951 | 0.015 |
| 6 | 388 | 0.992 | 0.892 | 0.955 | 0.015 | 285 | 1 | 0.895 | 0.954 | 0.015 |
| 7 | 121 | 0.982 | 0.895 | 0.951 | 0.015 | 167 | 1 | 0.892 | 0.954 | 0.015 |
| 8 | 128 | 0.985 | 0.887 | 0.950 | 0.017 | 113 | 0.979 | 0.849 | 0.950 | 0.015 |
| 9 | 767 | 0.996 | 0.898 | 0.958 | 0.016 | 276 | 1 | 0.897 | 0.952 | 0.015 |
| $\mu$ | 354 | 0.990 | 0.898 | 0.955 | 0.015 | 164 | 0.990 | 0.889 | 0.952 | 0.016 |
| $\sigma$ | 211 | 0.004 | 0.010 | 0.003 | 0.001 | 80 | 0.009 | 0.020 | 0.002 | 0.002 |

For the task study, FAUPA detections are expected for each subject, and the total number of FAUPAs across the whole brain is expected to vary from 63 to 285 with $\mu\pm\sigma=164\pm80$, which is significantly smaller than that of the resting-state study; showing the dependence of FAUPA on the brain functional state. The range of the mean is expected to be from 0.950 to 0.954 with a group $\mu\pm\sigma=0.952\pm0.002$, which is almost the same as the resting-state study. Thus demonstrating the almost perfect temporal correlation within each FAUPA that is independent of the brain functional state.

Figure 6A:
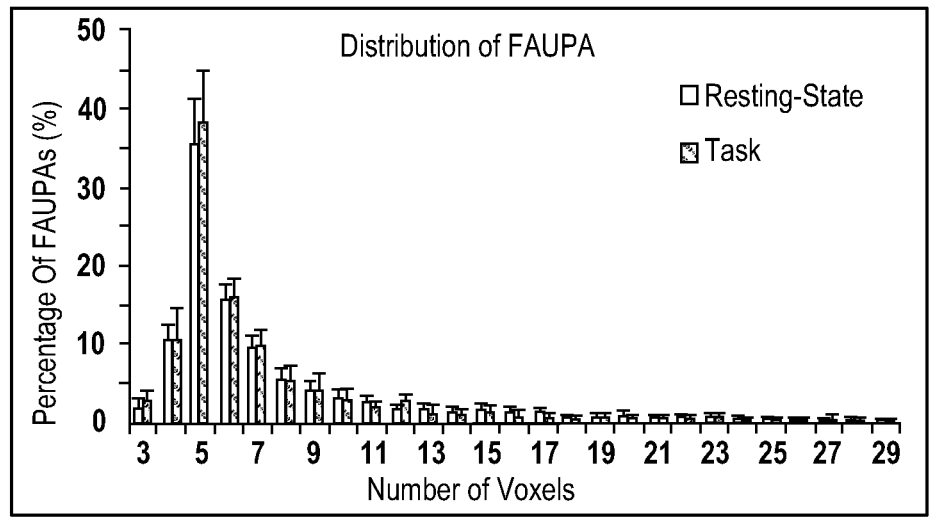
FIG. 6A is a histogram of group-mean FAUPAs as a function of the total number of voxels contained in a FAUPA for the resting-state study and the task study.
Figure 6B:
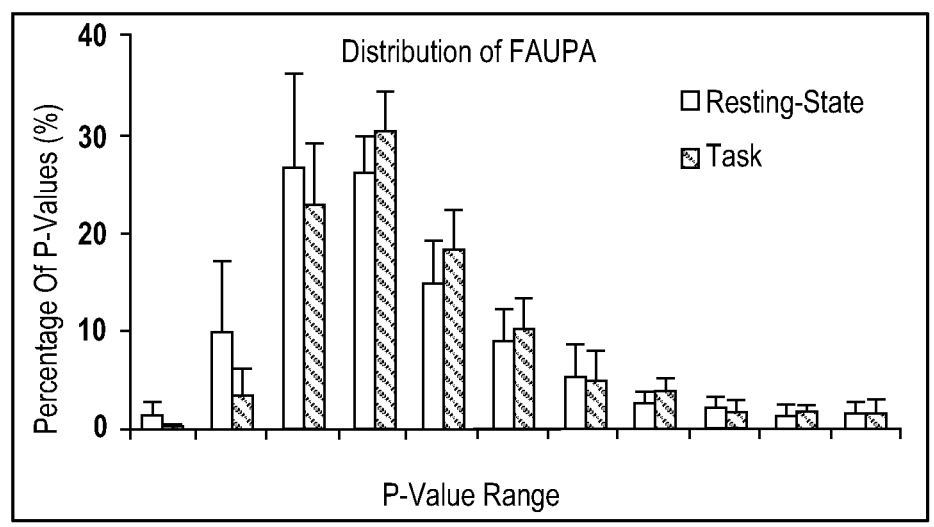
FIG. 6B is a histogram of group-mean P values as a function of P-value range for the resting-state study and the task study.

FIG. 6A illustrates a histogram of group-mean FAUPAs as a function of the total number of voxels contained in a FAUPA for the resting-state study and the task study, and FIG. 6B illustrates a histogram of group-mean P values as a function of P-value range for the resting-state study and the task study. The P values represent the significance levels of the testing of the separation of a FAUPA from its adjacent area for all FAUPAs as explained below. The error bars indicate the corresponding standard deviation.

Brain images can include colored clusters that indicate a FAUPA. Each colored cluster connected with voxels of the same color represents a FAUPA, and a total of 16 colors can be used to differentiate the FAUPAs. For the resting-state study, 435 FAUPAs are expected, and for the task study, 201 FAUPAs are expected. As illustrated in FIGS. 6A and 6B, the group-mean distribution of the task study is similar to that of the resting-state study.

To test the separation of a FAUPA from its adjacent area, a layer of one voxel width bordering the FAUPA was generated. This resulted in a representative adjacent area. To examine whether the signal time course (S(t)) in this adjacent area is significantly different from that of the FAUPA, the temporal correlation of a voxel's signal time course with the FAUPA's signal time course was computed for each voxel, and then the Pearson correlation coefficient values of the adjacent area are compared with those of the FAUPA. The corresponding P value is then used to determine the separation of the FAUPA from its adjacent area.

The FAUPA is considered to be significantly separated from its adjacent area when P is less than 0.05. FIG. 6B shows the histograms of the expected group-mean P values for the resting-state and task studies. For the task study, more than 99.95% of the expected P values were less than 0.05, thus showing that more than 99.95% of the identified FAUPAs are significantly separated from their adjacent areas. Similar expected results are obtained for the resting-state study. Specifically, more than 98.7% of the P values are expected to be less than 0.05, showing that more than 98.7% of the identified FAUPAs are expected to be significantly separated from their adjacent areas. Overall, more than 98.7% of the identified FAUPAs are expected to be significantly separated from their adjacent areas for both the resting-state and task studies.

Using the FAUPA and the signal change time course, one or more FAUPAs can be determined to be associated with a task. For example, for the finger-tapping task of the task study, a FAUPA in the left motor cortex with a signal time course that appears during the time that the finger-tapping task was being performed is associated with the task based on the assumption that the temporal variation was caused only by the finger-tapping task. This finger-tapping-associated FAUPA was identified for each subject and was located in the similar area of the left motor cortex across all nine subjects. All FAUPAs determined to be associated with a task compose a functional network that is specific to the task, i.e., a task-specific network.

Figure 7A:
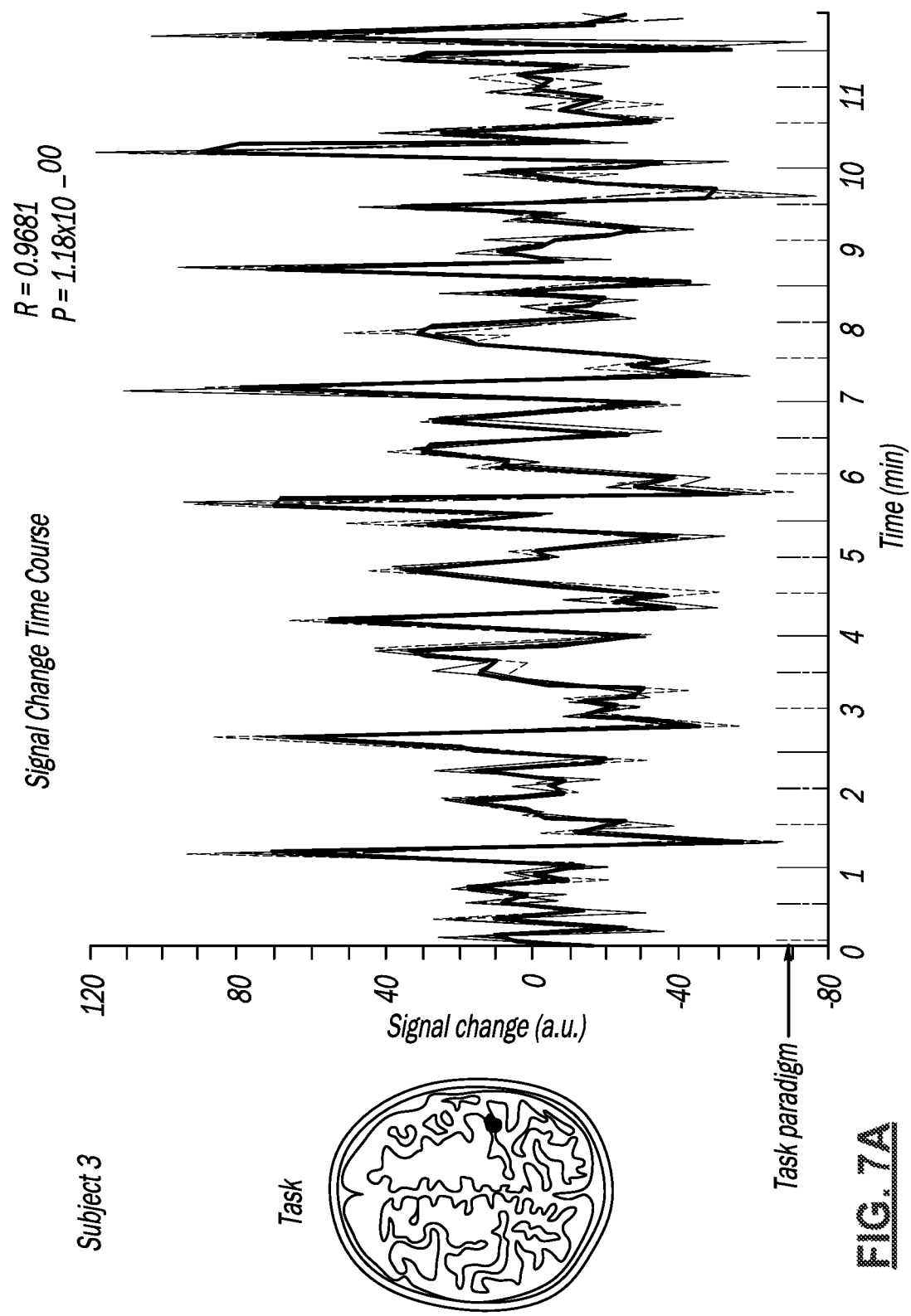
FIG. 7A illustrates a finger-tapping associated FAUPA and its corresponding signal time course for a test subject for the task study.
Figure 7B:
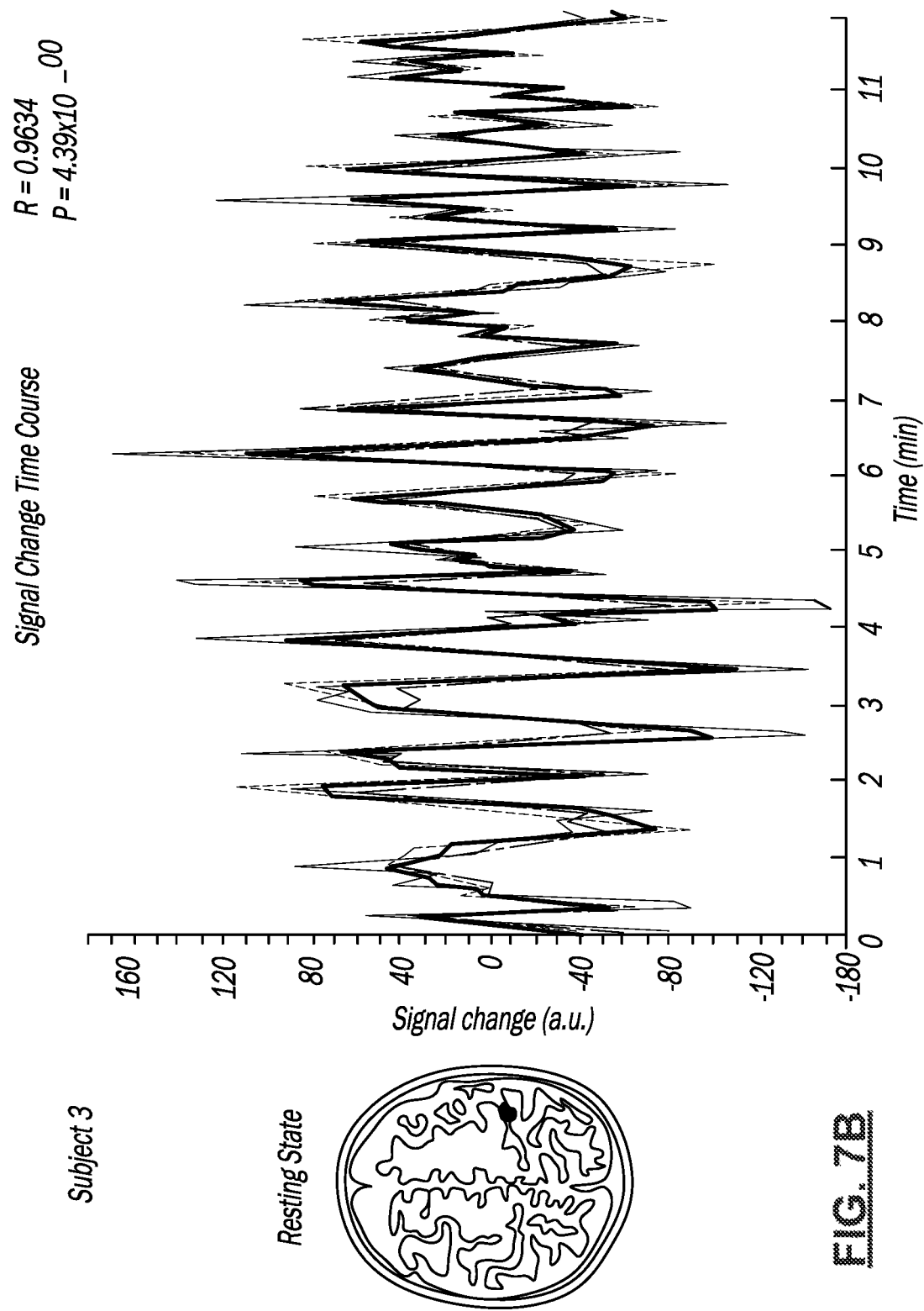
FIG. 7B illustrates an identified FAUPA and its corresponding signal time course in the same cortical area as the FAUPA in FIG. 7A for the test subject for the resting-state study.

FIGS. 7A-7B illustrate the expected results of subject 3 for the resting-state study and the task study. The left image in FIG. 7A illustrates the identified FAUPA in the left motor cortex for subject 3, indicated by the solid cluster, and this FAUPA contains a total of 6 voxels. The signal change time course was defined as $\Delta S_i(t)=S_i(t)-\overline{S}_i$, where $\overline{S}_i$ is the mean value of $S_i(t)$ over the 12-minute time period. The solid black line in the graph of FIG. 7A shows the FAUPA's $\overline{\Delta S}(t)$, and the dotted lines show $\Delta S_i(t)$ for the 6 voxels. All $\Delta S_i(t)$ are almost perfectly correlated with $\overline{\Delta S}(t)$, reflected in the FAUPA's mean $\overline{R}$ value $\mu \pm \sigma = 0.968 \pm 0.009$, thus showing the unitary pooled activity of the FAUPA. The first bar along the x-axis includes four tick marks. Each bar with four tick marks represents the onset of the reading words task and the duration of the task is 6 seconds. The second bar along the x-axis includes three tick marks. Each bar with three tick marks represents the onset of the viewing patterns task. The third bar along the x-axis is a solid tick mark. Each bar that is a solid tick mark represents the onset of the tapping right-hand fingers task. With the solid tick marks representing the onset of the finger-tapping task, a task-induced large signal change is present for each of the eight tasks.

Identifying a FAUPA located in a specific cortical area, such as the finger-tapping task associated FAUPA located in the finger representation area at the motor cortex (FIG. 7A), and using the FAUPA's $\overline{\Delta S}(t)$, the brain activity detection device 104 may be configured to determine one or more FAUPAs to be associated with this selected FAUPA. All FAUPAs determined to be associated with the selected FAUPA compose a FAUPA-based functional network. Analyzing the signal change of $\overline{\Delta S}(t)$ for each FAUPA within the network as a function of each task trial produces an activation change of the network from trial to trial. Computing the Pearson correlation coefficient of $\overline{\Delta S}(t)$ for all paired FAUPAs within the network as a function of each task trial produces a functional connectivity change of the network from trial to trial. Collating these two results produces a dynamic activity change of the network from trial to trial.

Identifying a new FAUPA that is not involved in the above described FAUPA-based functional network, and using this new FAUPA's $\overline{\Delta S}(t)$, the brain activity detection device 104 may be configured to determine one or more FAUPAs to be associated with this new FAUPA. All FAUPAs determined to be associated with this new FAUPA compose a new FAUPA-based functional network. Analyzing the signal change of $\overline{\Delta S}(t)$ for each FAUPA within this new network as a function of each task trial produces an activation change of the network from trial to trial. Computing the Pearson correlation coefficient of $\overline{\Delta S}(t)$ for all paired FAUPAs within the network as a function of each task trial produces a functional connectivity change of the network from trial to trial. Collating these two results produces a dynamic activity change of the new network from trial to trial. Repeating this procedure to determine all FAUPA-based functional networks and their associated dynamic network activity from trial to trial.

In FIG. 7B, the solid cluster in the left image indicates the location of the FAUPA identified during the resting-state study in the same area as that of the finger-tapping-associated FAUPA. The graphs illustrate the FAUPA's $\overline{\Delta S}(t)$ and $\overline{\Delta S}_i(t)$ of the first 8 listed voxels from the 22 voxels contained in the FAUPA.

Finger-tapping task associated FAUPA in the left motor cortex is detected for each of the nine subjects. To test the association of these nine FAUPAs with the finger-tapping task, an ideal response signal time course is generated based on the temporal paradigm of the finger-tapping task alone, using the 3dDeconvolve program in AFNI with the convolution kernel SPMG3. The signal change time course is first generated by subtracting the signal time course with its mean value and then comparing it with $\overline{\Delta S}(t)$ for the nine FAUPAs. The temporal correlation of $\overline{\Delta S}(t)$ with this ideal response signal change time course is computed for each FAUPA, and the R value ranged from 0.5414 (P=4.01×10−20) to 0.7694 (P=6.32×10−39) with $\mu \pm \sigma = 0.6951 \pm 0.0690$ (R=0.6951, P=4.08×10−32). The expected group-mean $\overline{\Delta S}(t)$ is almost perfectly correlated with the ideal response signal change time course, showing a statistically highly significant association of the expected FAUPAs with the finger-tapping task (R=0.9064, P=2.14×10−53).

Using the ideal response signal time course for a specific task, the brain activity detection device may be configured to determine one or more FAUPAs to be associated with the task. All FAUPAs determined to be associated with the task compose a task-specific network. Analyzing the signal change of $\overline{\Delta S}(t)$ for each FAUPA within this network as a function of each task trial produces an activation change of the network from trial to trial. Computing the Pearson correlation coefficient of $\overline{\Delta S}(t)$ for all paired FAUPAs within the network as a function of each task trial produces a functional connectivity change of the network from trial to trial. Collating these two results produces a dynamic activity change of the network from trial to trial.

Figure 8A:
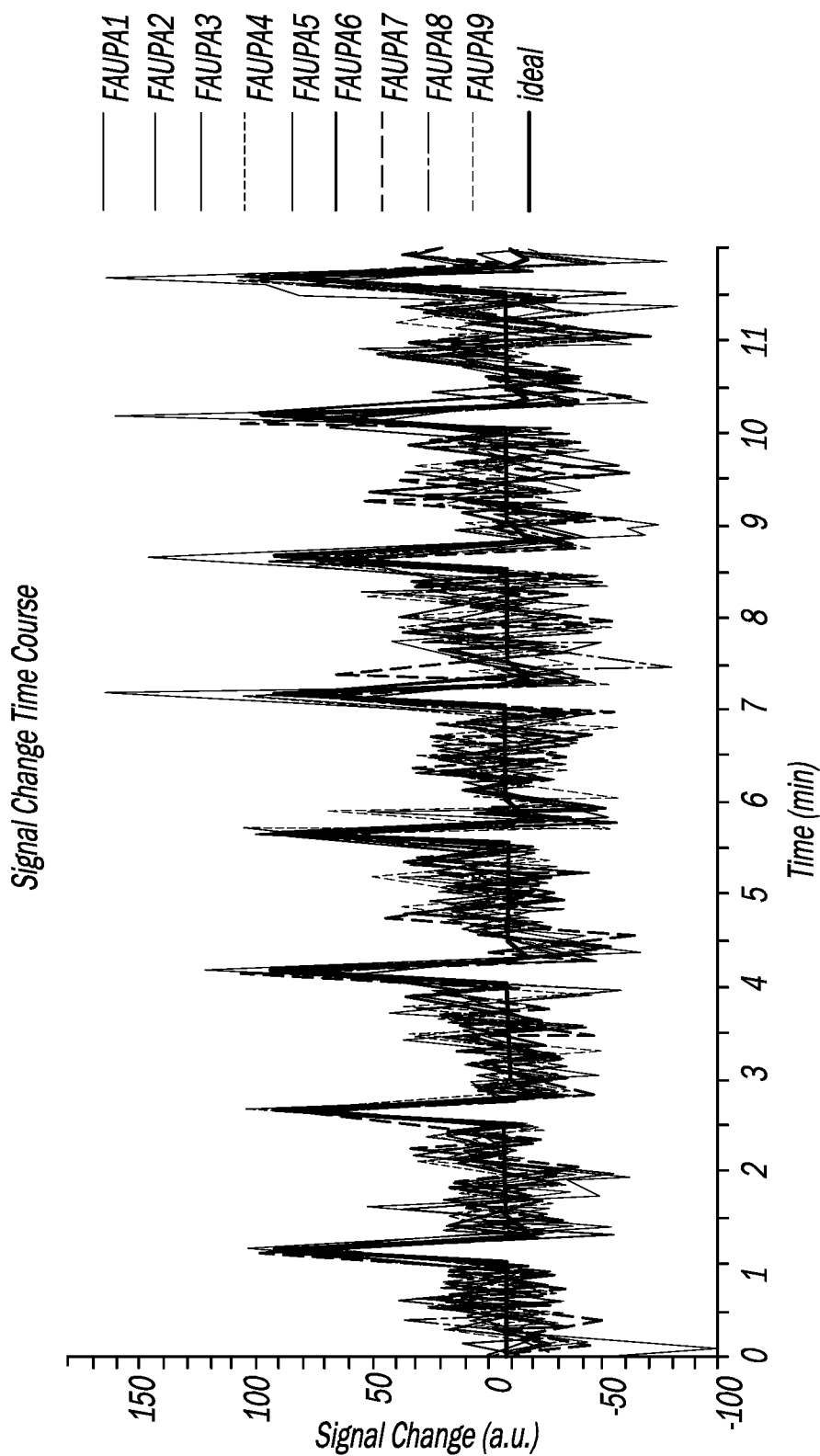
FIGS. 8A and 8B are graphs representing the change in BOLD signal over time for a finger-tapping associated task during the task study for the nine test subject.
Figure 8B:
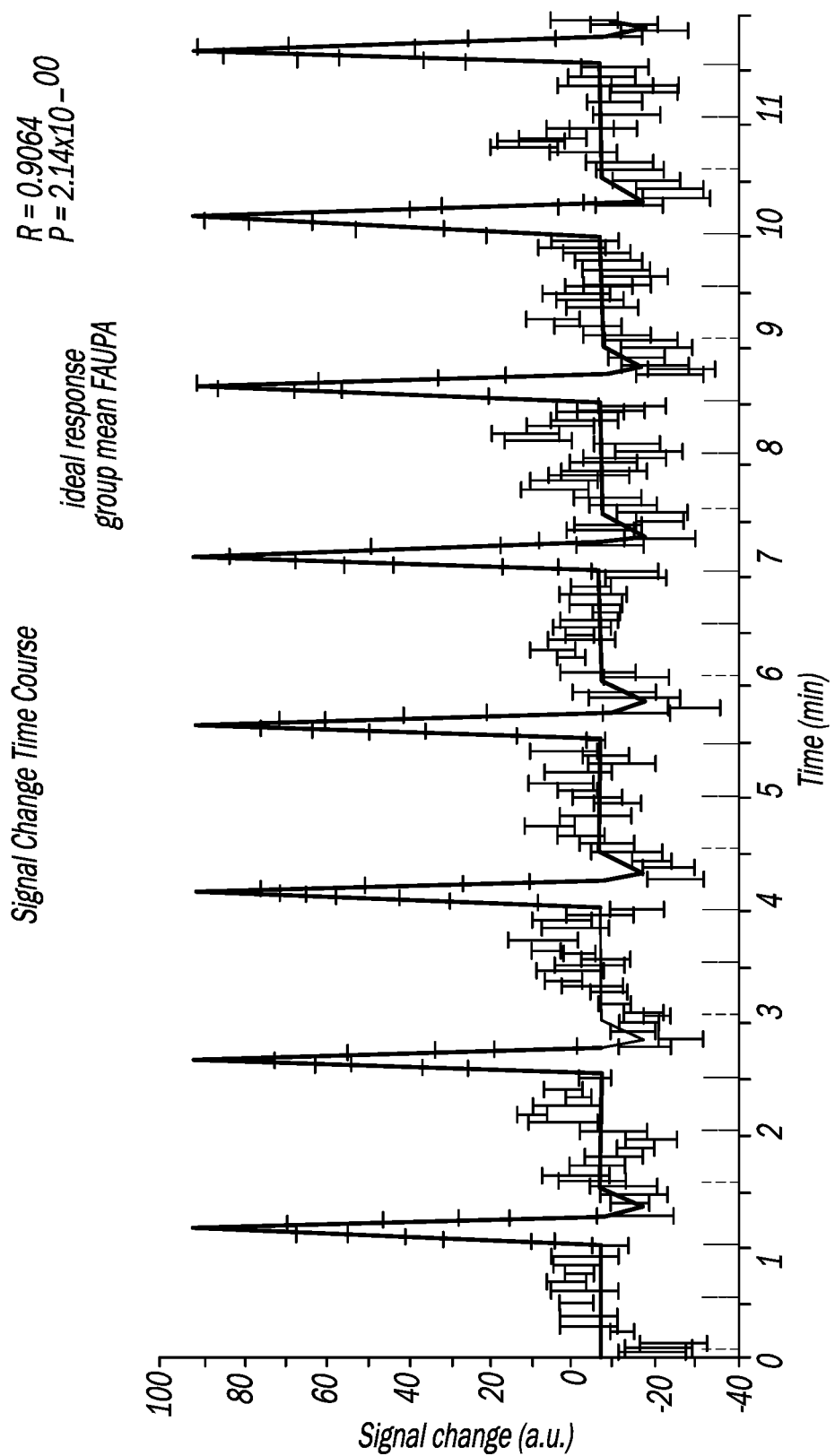

FIGS. 8A and 8B illustrate a graphical representation of the signal change over time for multiple test subjects. In FIG. 8A, the nine dotted lines represent the finger-tapping-associated FAUPAs' $\overline{\Delta S}(t)$ and the black solid line represents the finger-tapping-induced ideal response signal change time course. Each dotted line represents a different test subject. For example, FAUPA1 is a first test subject, FAUPA2 is a second test subject, FAUPA3 is a third test subject, FAUPA4 is a fourth test subject, FAUPA5 is a fifth test subject, FAUPA6 is a sixth test subject, FAUPA7 is a seventh test subject, FAUPA8 is an eighth test subject, and FAUPA9 is a ninth test subject.

In FIG. 8B, the dotted line represents the group mean of the nine FAUPAs' $\overline{\Delta S}(t)$ of FIG. 8A and the solid line represents the ideal response signal change time course. The expected temporal correlation of these two lines is almost perfect. The first bar along the x-axis includes three equally spaced tick marks. Each bar with three equally spaced tick marks represents the onset of the reading words task. The second bar along the x-axis includes three tick marks where the middle tick mark is smaller than the surrounding two tick marks, which represents the onset of the viewing patterns task. The third bar along the x-axis is a solid tick mark. Each bar that is a solid tick mark represents the onset of the tapping right-hand fingers task. The error bar indicates the standard error of the mean.

To further demonstrate the association of FAUPA with a task, four FAUPAs were selected from subject 9. One FAUPA is associated with the word-reading task, one FAUPA is associated with the pattern-viewing task, one FAUPA is associated with the finger-tapping task, and the last FAUPA is associated with all three of the tasks.

FIGS. 9A-9C illustrate the FAUPAs for all three tasks during the task study for Subject 9. FIG. 9A illustrates results for the word-reading associated FAUPA that contains 5 voxels. The right plot shows the 6 signal change time courses, where the black solid line represents the mean FAUPA's $\overline{\Delta S}(t)$ and the other 5 dotted lines for the 5 voxels. FIG. 9B illustrates the pattern-viewing-associated FAUPA that contained a total of 5 voxels. The solid cluster in the left image indicates the expected location of this FAUPA. The right plot shows the expected 6 signal change time courses, where the black solid line represents the expected FAUPA's $\overline{\Delta S}(t)$ and the other 5 dotted lines for the 5 voxels. FIG. 9C illustrates all three task-associated FAUPA that contained a total of 7 voxels. The solid cluster in the left image indicates the expected location of this FAUPA. The right plot shows the 8 signal change time courses, where the black solid line represents the expected FAUPA's $\overline{\Delta S}(t)$ and the other 7 dotted lines for the 7 voxels.

Figure 10A:
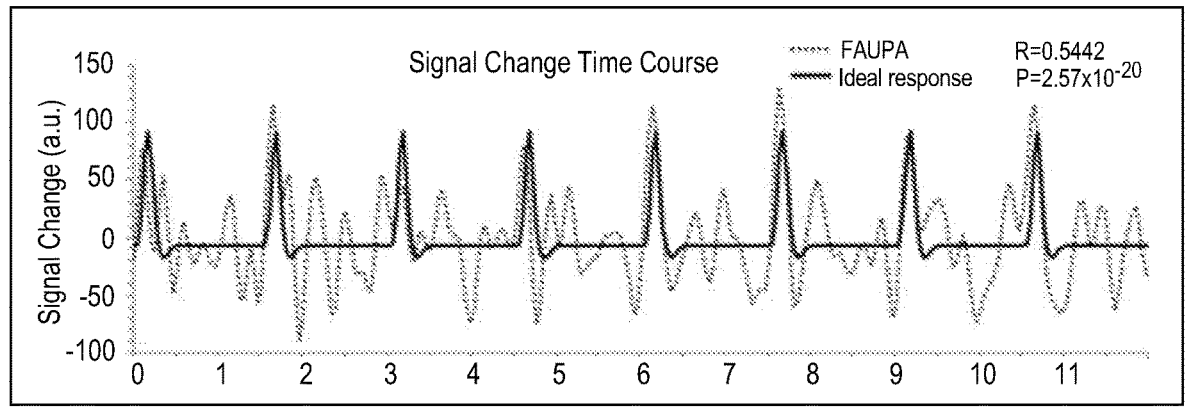
Figure 10B:
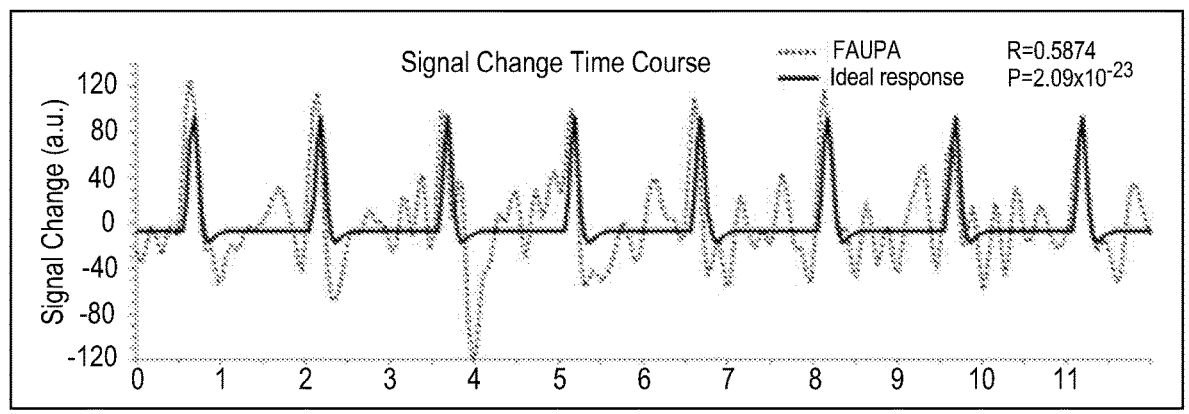

For each FAUPA, the expected temporal correlation of $\overline{\Delta S}(t)$ with its corresponding ideal response signal change time course is statistically highly significant (the minimum R=0.5414, the maximum P=4.01×10−20), showing a strong association of the FAUPA with the task. FIGS. 10A-10D compare the temporal correlation of task-associated signal change time course with the task-induced ideal response signal change time course for four tasks. In FIG. 10A, the dotted line represents the word-reading-associated FAUPA's $\overline{\Delta S}(t)$ (see also FIG. 9A), and the solid line represents the word-reading-induced ideal response signal change time course. In FIG. 10B, the dotted line represents the pattern-viewing-associated FAUPA's $\overline{\Delta S}(t)$ (see also FIG. 9B), and the solid line represents the pattern-viewing-induced ideal response signal change time course. In FIG. 10C, the dotted line represents the finger-tapping-associated FAUPA's $\overline{\Delta S}(t)$, and the solid line represents the finger-tapping-induced ideal response signal change time course. In FIG. 10D, the dotted line represents the FAUPA's $\overline{\Delta S}(t)$ that was associated with all three tasks (see also FIG. 9C), and the solid line represents the corresponding ideal response signal change time course. The first bar along the x-axis includes three equally spaced tick marks. Each bar with three equally spaced tick marks represents the onset of the reading words task. The second bar along the x-axis includes three tick marks where the middle tick mark is smaller than the surrounding two tick marks, which represents the onset of the viewing patterns task. The third bar along the x-axis is a solid tick mark. Each bar that is a solid tick mark represents the onset of the tapping right-hand fingers task.

For the fMRI scans taken during the resting-state study, an expected FAUPA was identified that overlapped with the finger-tapping-associated FAUPA for each subject. For example, FIG. 7B illustrates such a FAUPA in the similar area of the left motor cortex for subject 3, and this FAUPA contains a total of 22 voxels. The solid black line in the right plot shows the FAUPA's $\overline{\Delta S}(t)$, and the dotted lines show $\overline{\Delta S}_i(t)$ of the first 8 listed voxels from the 22 voxels, respectively. All expected $\overline{\Delta S}_i(t)$ are also almost perfectly correlated with $\overline{\Delta S}(t)$, reflected in the FAUPA's mean $\overline{R}$ value $\mu \pm \sigma = 0.963 \pm 0.014$, thus demonstrating the unitary pooled activity of the FAUPA. For these nine resting-state fMRI-identified FAUPAs, the R value of the temporal correlation of $\overline{\Delta S}(t)$ with the finger-tapping-induced ideal response signal change time course ranged from −0.1388 to 0.0795 with $\mu \pm \sigma = -0.0457 \pm 0.0809$ (R=−0.0457, P=0.44), reflecting the resting-state in which the subjects did not perform the finger-tapping task, though these FAUPAs overlapped with those finger-tapping-associated FAUPAs. Thus, further demonstrating the dependence of FAUPA on the brain functional state. This shows that different FAUPAs can be formed in the same cortical area for different brain functional states.

Using an area's mean signal time course (seed function) to compute its correlation coefficient with each voxel's signal time course for the whole brain, and then thresholding $R_i$ with a chosen threshold value yields a functional connectivity map that shows those other brain areas that are functionally connected with the area. For the resting-state study, the fMRI-identified FAUPA's $\overline{\Delta S}(t)$ and each voxel's $\overline{\Delta S}_i(t)$ are used to generate a motor-cortex-associated functional connectivity map during the resting-state, with an arbitrarily selected threshold R=0.5 (P=3.6×10−17). A motor cortex associated functional connectivity map can illustrate clusters. The clusters can be colored or bright and show the areas functionally connected with the motor cortex during the resting state at the chosen significance level. These functional connectivity maps demonstrate a large inter-subject variation, showing a subject-dependent motor-cortex-associated functional connectivity map during the resting state.

An expected functional connectivity map was generated for the finger-tapping-associated FAUPA in the same motor cortex. This functional connectivity map is specifically associated with the right-hand five-finger representation area in the left motor cortex. The map shows dramatically less and more concentrated clusters across the whole brain in comparison to that of the resting-state, and these clusters were involved in the performance of the finger-tapping task. Similar expected results were observed for the other eight subjects. The fact that more clusters appeared in the functional connectivity maps for the resting state, such as that in the visual cortex, suggests that more functional networks were involved in the resting state than in the state when performing the finger-tapping task.

In the studies performed, the total number of voxels contained in a FAUPA varied from 3 to 29, and there were about 35% of the FAUPAs containing five voxels each, followed by ~15% containing six voxels, etc. (FIG. 6A). In this study, the isotropic voxel had a size of 3.5 mm. For an isotropic FAUPA with eight voxels, its size would be 7 mm. Accordingly, the size of FAUPA is at a length scale of several millimeters for most FAUPAs.

The separation of an expected FAUPA from its adjacent area is verified by testing the temporal correlation of the signal time courses between the FAUPA and its adjacent area. More than 99% of the identified FAUPAs showed a significant difference from their adjacent areas for both the resting-state study and the task study.

The association of FAUPA with a task is first verified by testing the temporal correlation of the finger-tapping-associated FAUPA's $\overline{\Delta S}(t)$ with the finger-tapping-induced ideal response signal change time course at both the individual level and the group level (FIGS. 8A and 8B). At the individual level, each of the eight finger-tapping tasks induces a large signal change that is significantly correlated with the task for each individual subject (the minimum R=0.5414, the maximum P=4.01×10−20) (FIG. 8A). At the group level, the group-mean $\overline{\Delta S}(t)$ is almost perfectly correlated with the finger-tapping-induced ideal response signal change time course for each of the eight finger-tapping tasks (R=0.9064, P=2.14×10−53) (FIG. 8B). These expected results suggest a potential of using FAUPA's $\overline{\Delta S}(t)$ to investigate the FAUPA's response to each trial (i.e., a trial-level study for each individual subject). For example, if a subject missed a task (e.g., the subject did not tap fingers during the trial), the FAUPA's $\overline{\Delta S}(t)$ would show the lack of a finger-tapping-induced large signal change for that trial without having a priori knowledge whether the subject missed the trial and which trial the subject missed.

The association of expected FAUPAs with tasks is further verified with three additional FAUPAs that are associated with three different tasks: (1) word-reading alone (FIG. 10A); (2) pattern-viewing alone (FIG. 10B); and (3) word-reading, pattern-viewing, and finger-tapping (FIG. 10D), respectively. Again, for each task, the task-associated FAUPA's $\overline{\Delta S}(t)$ shows a significant correlation with the task-induced ideal response signal change time course (the minimum R=0.5442, the maximum P=2.57×10−20). The plots in FIGS. 10A-10D provide further expected evidence to support the suggestion that it might be possible to use FAUPA's $\overline{S}(t)$ to investigate the FAUPA's response to each trial for each individual subject.

Performing any functional task requires dynamically mediated activities of many brain areas, and the investigation of functional connectivity maps may play a key role in understanding the brain functional network for a specific task. Using FAUPA's $\overline{\Delta S}(t)$ generates an objective functional connectivity map that is associated with the FAUPA. With the locations of these resting-state fMRI-identified FAUPA being in a similar area of the left motor cortex and the FAUPA being objectively identified, the large variations in these functional connectivity maps demonstrate a subject-dependent functional connectivity map. These subject-dependent functional connectivity maps might reflect different brain activities during the resting state, though all the subjects were asked to perform the same task. It should be noted that the resting state is not a well-controlled task state because it is very difficult for the subjects to concentrate on that one task for that long of a period of time (e.g., 12 min.). This result suggests a potential of using FAUPA's $\overline{\Delta S}(t)$ to investigate functional connectivity map at the individual subject level.

Task-associated functional connectivity maps clearly illustrate that different functional connectivity maps are associated with different tasks. These maps may be used to investigate functional networks associated with specific tasks.

The FAUPA has the following characteristics: (1) it is a dynamic neural activity-associated functional area that is separated from its adjacent area; (2) the underlying pooled activity is a dynamically unitary activity across the entire area; (3) this unitary activity is characterized by a generic time function G(t) that relates to the FAUPA's $\overline{S}(t)$ via $\overline{S}(t)=\overline{C}\cdot G(t)+\overline{\delta}(t)$; (4) FAUPA is brain functional state dependent; (5) different FAUPA can be formed in the same cortical area for different functional states; and (6) the size of FAUPA is at a spatial scale of several millimeters.

The determination of FAUPA is objective and automatic with no requirement of a priori knowledge of the activity-induced ideal response signal time course. This determination is based on the following assumption: the temporal variation of the underlying pooled activity is the same across the entire area (i.e., the pooled activity is a dynamically unitary activity). This assumption implies a near perfect temporal correlation everywhere (i.e., $\overline{R}=1$). The assumption was verified by the observed $\overline{R}$ values of the identified FAUPA. For the resting state, the range of the mean $\overline{R}$ values was from 0.949 to 0.959 with a group $\mu\pm\sigma=0.955\pm0.003$ for the nine subjects (Table 1). For the task state, the range was from 0.949 to 0.954 with a group $\mu\pm\sigma=0.952\pm0.002$, which is similar to that of the resting state. This almost perfect temporal correlation across the entire area shows that the underlying pooled activity is indeed a dynamically unitary activity, and the FAUPA's signal time course measures this pooled activity.

Based on the foregoing, the brain detection device not only identifies FAUPAs within the brain, but also determines different networks and dynamic activity. For example, the brain activity detection device may be configured to identify FAUPA based functional network in a brain of a living object. Specifically, the device may be configured to: select a FAUPA from among a plurality of identified FAUPA; compute Pearson correlation coefficient of the selected FAUPA based on the signal time course of the selected FAUPA with signal time course of all other identified FAUPAs; determine that one or more FAUPAs are associated with the selected FAUPA in response to the Pearson correlation coefficient of the one or more FAUPAs being greater than a first threshold; and identify the selected FAUPA and the associated FAUPAs as a FAUPA-based functional network.

The brain activity detection device may also be configured to identify all FAUPA-based functional networks in a brain of a living object. Specifically, the device 104 may classify the identified FAUPAs in multiple groups, such that the FAUPAs of a given group have a Pearson correlation coefficient that satisfies a predetermined condition. For example, a first group of FAUPAs may have a Pearson correlation coefficient within a first range (e.g., R<ThA), a second group of FAUPAs may have a Pearson correlation coefficient between a second range (ThA<R<ThB), a third group of FAUPAs may have Pearson correlation coefficient between a third range (ThB<R<ThC), and so on and so forth. ThA, ThB, and ThC may be the same or not. Each group may then be identified as a FAUPA-based functional network. The brain activity detection device may store each range, and the thresholds of the range may be adjusted by the operator via a user interface.

The brain activity detection device may also be configured to determine dynamic activity of FAUPA-based functional networks in a brain of a living object. Specifically, the device may be configured to: identify a FAUPA-based functional network responsible; evaluate the cortical activation and functional connectivity of the signal time courses of all FAUPAs within this FAUPA-based functional network as a function of time; and identify these changes in the cortical activation and functional connectivity as the dynamic activity of the FAUPA-based functional network.

The brain activity detection device may also be configured to identify task-associated FAUPAs in a brain of a living object. Specifically, the brain activity detection may be configured to: generate a task-induced ideal response signal time course; identify FAUPAs associated with the task satisfying a predetermined condition, where the Pearson correlation coefficient of the task-induced ideal response signal time course with the FAUPA's signal time course satisfy a predetermined condition; and identify these FAUPAs as task-associated FAUPAs in response to the task.

The brain activity detection device may also be configured to identify a task-specific network in a brain of a living object. Specifically, the device may be configured to identify one or more FAUPAs associated with a specific task; and identify these FAUPAs as the task-specific network responsible for the task.

The brain activity detection device may also be configured to determine dynamic activity of task-specific networks in a brain of a living object. Specifically, the device may be configured to: identify a task-specific network responsible for a specific task; evaluate the cortical activation and functional connectivity of the signal time courses of all FAUPAs within the task-specific network as a function of task trial; and identify these changes in the cortical activation and functional connectivity as the dynamic activity of the task-specific network when performing the task from trial to trial.

The foregoing description of the embodiments has been provided for purposes of illustration and description. It is not intended to be exhaustive or to limit the disclosure. For example, the brain activity detection device may include programs other than AFNI programs to refine the images from the MRI scanner. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough and will fully convey the scope to those who are skilled in the art. Numerous specific details are set forth, such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail.

The term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip. While various embodiments have been disclosed, other variations may be employed. All of the components and function may be interchanged in various combinations. It is intended by the following claims to cover these and any other departures from the disclosed embodiments which fall within the true spirit of this invention.

What is claimed is:

1. A method for identifying a functional network in a brain of a living object, the method comprising:
   acquiring a plurality of images of the brain over a predetermined period using an image processor, wherein during the predetermined period the living object is performing a task, and wherein the plurality of images of the brain include a plurality of voxels;
   selecting a given voxel from the plurality of voxels;
   iteratively forming a stable region of interest by
   h) forming a first region of interest from the given voxel;
   i) selecting a group of voxels from the plurality of voxels, where the group of voxels surround the first region of interest and includes voxels which do not border the first region of interest;
   j) calculating a similarity measure for each voxel in the group of voxels; and
   k) forming a second region of interest by adding voxels from the group of voxels to the first region of interest, where the added voxels have a similarity measure that exceeds a first threshold and the first threshold is a statistical criterion derived from the first region of interest;
   l) replacing the first region of interest with the second region of interest and
   m) repeating steps h)-l) until the number of voxels in the first region of interest equals the number of voxels in the second region of interest
   identifying the stable region of interest as a functional area of unitary pooled activity by comparing temporal behavior of voxels in the stable region of interest to voxels bordering the stable region of interest;

identifying areas that are functionally connected to the functional area of unitary pooled activity;

grouping the identified functionally connected areas as included in the functional network; and displaying the functional network;

wherein identifying the stable region of interest as a functional area of unitary pooled activity includes determining a second threshold;

identifying voxels that border the stable region of interest;

for each identified voxel, calculating a similarity measure for the given voxel;

determining a number of identified voxels having a similarity measure greater than the second threshold but less than the first threshold;

identifying the stable region of interest as a functional area of unitary pooled activity when the number of identified voxels having a similarity measure greater than the second threshold but less than the first threshold is less than a fixed percentage of voxels bordering the stable region of interest.

2. The method of claim 1 wherein the similarity measure is further defined as Pearson correlation coefficient.

3. The method of claim 2 further comprising:

calculating a voxel threshold; and selecting the second region of interest from the plurality of voxels in response to:
  (i) the number of voxels in the second region of interest being greater or less than the number of voxels in the first region of interest; and
  (ii) the number of voxels in the second region of interest being greater than the voxel threshold.

4. The method of claim 2 further comprising:

maintaining a number of iterations count; and selecting the second region of interest from the plurality of voxels in response to:
  (i) the number of voxels in the second region of interest being greater or less than the number of voxels in the first region of interest; and
  (ii) the number of iterations count exceeding an iteration threshold.

5. The method of claim 2 wherein the first threshold is calculated based on the first region of interest, including: (i) a mean signal time course, (ii) a first region of interest Pearson correlation coefficient, (iii) a mean, and (iv) a standard deviation.

6. A non-transitory computer-readable medium storing processor-executable instructions, the instructions comprising:

acquiring a plurality of images over a predetermined period of time using functional magnetic resonance imaging (fMRI) system;

selecting a given voxel from the plurality of voxels;

iteratively forming a stable region of interest by
  n) forming a first region of interest from the given voxel;
  o) selecting a group of voxels from the plurality of voxels, where the group of voxels surround the first region of interest;
  p) calculating a similarity measure for each voxel in the group of voxels; and
  q) forming a second region of interest by adding voxels from the group of voxels to the first region of interest, where the added voxels have a similarity measure that exceeds a first threshold and the first threshold is a statistical criterion derived from the first region of interest;
  r) replacing the first region of interest with the second region of interest and
  s) repeating steps n)-r) until the number of voxels in the first region of interest equals the number of voxels in the second region of interest identifying the stable region of interest as a functional area of unitary pooled activity by determining a second threshold;

identifying voxels that border the stable region of interest;

for each identified voxel, calculating a similarity measure for the given voxel;

determining a number of identified voxels having a similarity measure greater than the second threshold but less than the first threshold;

identifying the stable region of interest as a functional area of unitary pooled activity when the number of identified voxels having a similarity measure greater than the second threshold but less than the first threshold is less than a fixed percentage of voxels bordering the stable region of interest; and displaying, via a display device, the functional area of unitary pooled activity.

7. The non-transitory computer-readable medium of claim 6 wherein the similarity measure is further defined as Pearson correlation coefficient.

8. The non-transitory computer-readable medium of claim 7 further comprising:

calculating a voxel threshold; and selecting the second region of interest from the plurality of voxels in response to:
  (i) the number of voxels in the second region of interest being greater or less than the number of voxels in the first region of interest; and
  (ii) the number of voxels in the second region of interest being greater than the voxel threshold.

9. The non-transitory computer-readable medium of claim 7 further comprising:

maintaining a number of iterations count; and selecting the second region of interest from the plurality of voxels in response to:
  (i) the number of voxels in the second region of interest being greater or less than the number of voxels in the first region of interest; and
  (ii) the number of iterations count exceeding an iteration threshold.

10. The non-transitory computer-readable medium claim 7 wherein the first threshold is calculated based on the first region of interest, including: (i) a mean signal time course, (ii) a first region of interest Pearson correlation coefficient, (iii) a mean, and (iv) a standard deviation.

* * * * *